(12) United States Patent
Smith

(10) Patent No.: US 8,986,319 B2
(45) Date of Patent: Mar. 24, 2015

(54) SCREW HEAD LOCKER APPARATUS AND METHODS OF USE

(75) Inventor: Ketchen Smith, Escondido, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 248 days.

(21) Appl. No.: 13/270,405

(22) Filed: Oct. 11, 2011

(65) Prior Publication Data

US 2012/0089150 A1    Apr. 12, 2012

Related U.S. Application Data

(60) Provisional application No. 61/391,281, filed on Oct. 8, 2010.

(51) Int. Cl.
| | |
|---|---|
| *A61B 17/58* | (2006.01) |
| *A61B 17/60* | (2006.01) |
| *A61F 2/00* | (2006.01) |
| *A61B 17/70* | (2006.01) |

(52) U.S. Cl.
CPC .......... *A61B 17/7076* (2013.01); *Y10S 606/916* (2013.01)
USPC .......................................... 606/104; 606/916

(58) Field of Classification Search
USPC ................. 606/86 R, 86 A, 90, 104, 916; 81/451–455
See application file for complete search history.

(56) References Cited

U.S. PATENT DOCUMENTS

| | | | |
|---|---|---|---|
| 2,905,215 A * | 9/1959 | Hlynsky | 81/455 |
| 7,481,813 B1 * | 1/2009 | Purcell | 606/86 R |
| 2005/0119667 A1 | 6/2005 | Leport et al. | |
| 2005/0131408 A1 | 6/2005 | Sicvol et al. | |
| 2005/0149036 A1 | 7/2005 | Varieur | |
| 2009/0082809 A1 | 3/2009 | Nguyen et al. | |
| 2009/0228054 A1 * | 9/2009 | Hoffman et al. | 606/86 A |
| 2009/0264896 A1 | 10/2009 | Biedermann et al. | |

* cited by examiner

*Primary Examiner* — Andrew Yang
*Assistant Examiner* — Diana S Jones
(74) *Attorney, Agent, or Firm* — Michael J. Loi

(57) ABSTRACT

An apparatus for provisionally locking a polyaxial head on a fixed head of a bone screw using a locking bushing includes an elongated housing with a proximal end and a distal end, the distal end having couplers for releasably coupling with the polyaxial head; an inner shaft slidably engaged within the housing and including a distal portion, a middle portion, and a proximal portion; and an actuator that selectively positions the inner shaft within the housing to engage at least one of the distal portion, the middle portion, and the proximal portion with at least one of the couplers and the bushing disposed between the distal portion and the fixed head of the bone screw.

10 Claims, 6 Drawing Sheets

SCREW HEAD LOCKER APPARATUS AND METHODS OF USE

CROSS-REFERENCE TO RELATED APPLICATIONS

This application claims priority to U.S. Provisional Patent Application No. 61/391,281, filed Oct. 8, 2010, which is incorporated herein by reference.

FIELD

The present invention relates generally to an apparatus and method for internal fixation of the spine and more specifically, to provisionally locking a polyaxial head on a fixed head of a bone screw using a locking bushing.

BACKGROUND

Certain spinal conditions, including a fracture of a vertebra and a herniated disc, indicate treatment by spinal immobilization. Several methods of spinal immobilization are known, including surgical fusion and the attachment of pins and bone plates to the affected vertebras.

Spinal immobilization systems typically require the threaded securement of some form of bone anchor and the like or bone screw-assembly into two or more vertebrae, which entails drawing the rod to the anchors/screw-assemblies or drawing the anchors/screw-assemblies to the rod. Spinal screw-assemblies are used to secure a stabilization rod and comprise various components including a pedicle screw and a body member. The design of the spinal screw-assemblies allows for variable angular movement of the body member with respect to the pedicle screw with a threaded shaft portion of the screw extending through an opening in an end of the body member. However, in these systems, in order to tighten the spinal screw-assembly at a specific angle, a rod, and set screw must first be inserted, the components are tightened, and then the rod and set screw are removed.

SUMMARY

Provided herein are apparatuses, systems, and methods of use for provisionally locking a polyaxial head on a fixed head of a bone screw using a locking bushing. In one example, the apparatus for locking the polyaxial head on the fixed head of the bone screw using the locking bushing includes an elongated housing with a proximal end and a distal end, the distal end having couplers for releasably coupling with the polyaxial head; an inner shaft slidably engaged within the housing and including a distal portion, a middle portion, and a proximal portion; and an actuator that selectively positions the inner shaft within the housing to engage at least one of the distal portion, the middle portion, and the proximal portion with at least one of the couplers and the bushing disposed between the distal portion and the fixed head of the bone screw.

In other features, the distal portion includes a first diameter, the middle portion includes a second diameter greater than the first diameter, and the proximal portion includes a third diameter greater than the second diameter. In still other features, the actuator positions the inner shaft in a first position to engage the proximal portion with a proximal tip of the couplers to lock the polyaxial head with a distal end of the couplers. The actuator positions the inner shaft in a second position to engage the middle portion with the proximal tip of the couplers to release the polyaxial head from the distal end of the couplers. The distal portion engages the locking bushing in the first position. The distal portion forces the bushing into frictional engagement between the fixed head of the screw and the polyaxial head.

In yet other features, the actuator includes a lever pivotably coupled to the proximal end of the barrel with a first end operably linked with the inner shaft and a second end with a handle. In still other features, the apparatus further includes tensioned bars that bias proximal tips of the couplers towards the inner shaft. The distal ends of the couplers include protrusions extending towards the inner shaft configured to engage with mating pockets in the polyaxial head. The couplers include a pair of tangs pivotably coupled to the distal end of the barrel.

In another example, the apparatus for provisionally locking the polyaxial head on the fixed head of the bone screw using the locking bushing includes a barrel with a proximal end and a distal end; one or more tangs pivotally coupled to the distal end of the barrel, each including a proximal tip and a distal tip having a protrusion for releasably coupling with a pocket in the polyaxial head; an inner shaft slidably engaged within the barrel and including a distal portion with a first diameter, a middle portion with a second diameter greater than the first diameter, and a proximal portion with a third diameter greater than the second diameter; one or more tensioned bars on the distal end of the barrel configured to bias each proximal tip of each tang towards the inner shaft; and an actuator that selectively positions the inner shaft within the barrel to engage at least one of the distal portion, the middle portion, and the proximal portion with at least one of the tangs and the bushing disposed between the distal portion and the fixed head of the bone screw.

In other features, the actuator advances the inner shaft to engage the proximal portion with the proximal tip of the tang to rotate the distal tip of the tang towards the polyaxial head and engage the protrusion with the pocket. The actuator retracts the inner shaft to engage the middle portion with the proximal tip and allow the tensioned bar to bias the proximal tip towards the inner shaft such that the distal tip releases the protrusion from the pocket. The distal portion engages a proximal surface of the bushing and forces the bushing to frictionally engage between the polyaxial head and the fixed head of the screw. The actuator comprises a lever pivotably coupled to the proximal end of the barrel with a first end operably linked with the inner shaft and a second end including a handle.

In another example, a method for provisionally locking the polyaxial head on the fixed head of the bone screw with the locking bushing includes the steps of positioning an elongated housing with a proximal end and a distal end with couplers onto the polyaxial head; slidably engaging an inner shaft within the housing, the inner shaft including a distal portion, a middle portion, and a proximal portion; and selectively positioning the inner shaft within the housing to engage at least one of the distal portion, the middle portion, and the proximal portion with at least one of the couplers and the bushing disposed between the distal portion and the fixed head of the bone screw.

In other features, the method further includes the steps of positioning the inner shaft in a first position to engage the proximal portion with a proximal tip of the couplers to lock the polyaxial head with a distal end of the couplers; positioning the inner shaft in a second position to engage the middle portion with the proximal tip of the couplers to release the polyaxial head from the distal end of the couplers; engaging the distal portion with the bushing in the first position; and forcing the bushing into frictional engagement between the fixed head of the screw and the polyaxial head.

The apparatuses, systems, and methods of use are set forth in part in the description which follows, and part will be obvious from the description or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The words proximal and distal are applied to denote specific ends of components of the current invention described herein. A proximal end refers to the end of a component nearer to a medical professional when operating the component. A distal end refers to the end of the component further from the medical professional when operating the component.

The present invention helps to expedite the time of surgery by allowing a medical professional to provisionally tighten the spinal screw-assembly at a specific angle prior to placing a rod or set screw into the body member.

Figure 1:
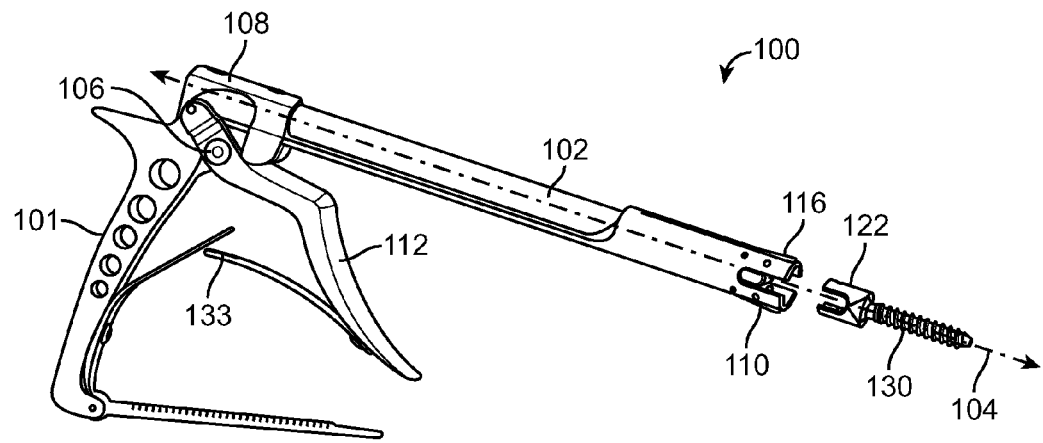
FIG. 1 is a perspective view of an exemplary apparatus for provisionally locking a polyaxial head on a fixed head of a bone screw using a locking bushing according to the principles of the present disclosure.

As shown in FIG. 1, a screw head locker apparatus 100 for provisionally locking a polyaxial head on a fixed head of a bone screw using a locking bushing generally comprises an elongated housing or barrel body 102 having a generally longitudinal axis 104, wherein the barrel body 102 includes a proximal end 108 and a distal end 110 generally along the longitudinal axis 104. A handle 101 extends downwardly from the proximal end 108 of the barrel body 102 for holding the screw head locker 100 by an operator. A trigger pin 106 is operably coupled to the barrel body 102 near the proximal end 108 of the barrel body 102. The trigger pin 106 may be coupled to the barrel body 102 by any suitable method of attachment such as, for example, a fastener, an aperture, a nut or bolt connection, or the like. An actuator, such as lever 112 rotatably associates with the trigger pin 106 and the lever 112 may extend from the trigger pin 106 via mechanical attachment by any suitable method of attachment, for example, a fastener, an aperture, a nut-bolt connection, a washer, or the like. Alternatively, the lever 112 and trigger pin 106 may be a unitary element that is mounted on the proximal end 108 of the barrel body 102.

Figure 2:
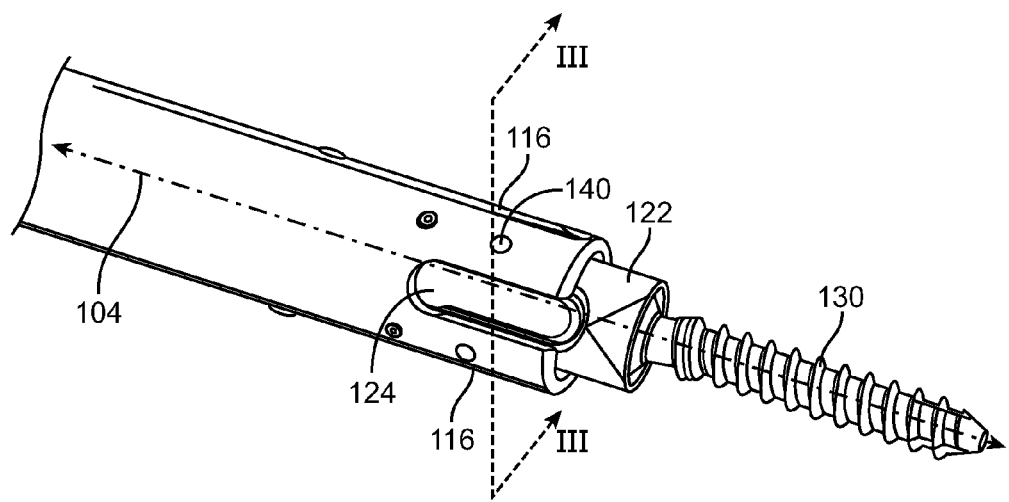
FIG. 2 is an enlarged perspective view of a distal end of the apparatus in FIG. 1 when the polyaxial head is engaged with the apparatus according to the principles of the present disclosure.

As shown in FIGS. 1 and 2, the distal end 110 of the barrel body 102 includes an opening to fit a polyaxial head such as screw body member 122 and a bone screw 130. The distal end 110 may further includes a plurality of tabs 140 positioned on the interior surface of the distal end 110, such that the screw body member 122 may be seated in the distal end 110 of the barrel body 102 and the proximal portion of the screw body member 122 may abut the tabs 140 and position the screw body member 122 to be locked within the distal end 110. The distal end 110 of the barrel body 102 includes a pair of couplers, such as tangs 116 that generally project along the longitudinal axis 104 and towards the distal end of the barrel body 102. The tangs 116 are operably associated with the trigger pin 106 and the lever 112 to secure and lock the screw body member 122 in the distal end 110 of the barrel body 102, as shown in FIG. 2. The barrel body 102 and the tangs 116 may be made from any suitable material as known in the art including, by way of example and not limitation, stainless steel, a thermoplastic or other materials. The barrel body 102 is generally cylindrical in shape; however, it may assume alternative shapes such as square, rectangular, polygonal, and the like.

Referring to FIGS. 1-3B, the tangs 116 are operably attached to the lever 112 via an inner shaft 124, discussed below, such that actuation of the lever 112 causes distal ends 119 of the tangs 116 to be axially displaced away or towards the longitudinal axis 104 by features on the shaft 124. In a first embodiment, actuation of the lever 112 causes the distal ends 119 of the tangs 116 to move inward or towards the longitudinal axis 104. In a second embodiment, actuation of the lever 112 causes the proximal ends of the tangs 116 to axially move inward or towards the longitudinal axis 104. In the first and second embodiments, returning the shaft 124 to its original position causes the tangs 116 to return to their original positions. In a further embodiment, a spring member 133 is operably coupled to the lever 112 and the handle 101, such that the spring member 133 urges the lever 112 from an actuated position back to its original position subsequent to actuation of the lever 112 in either the proximal or distal direction.

Figure 3A:
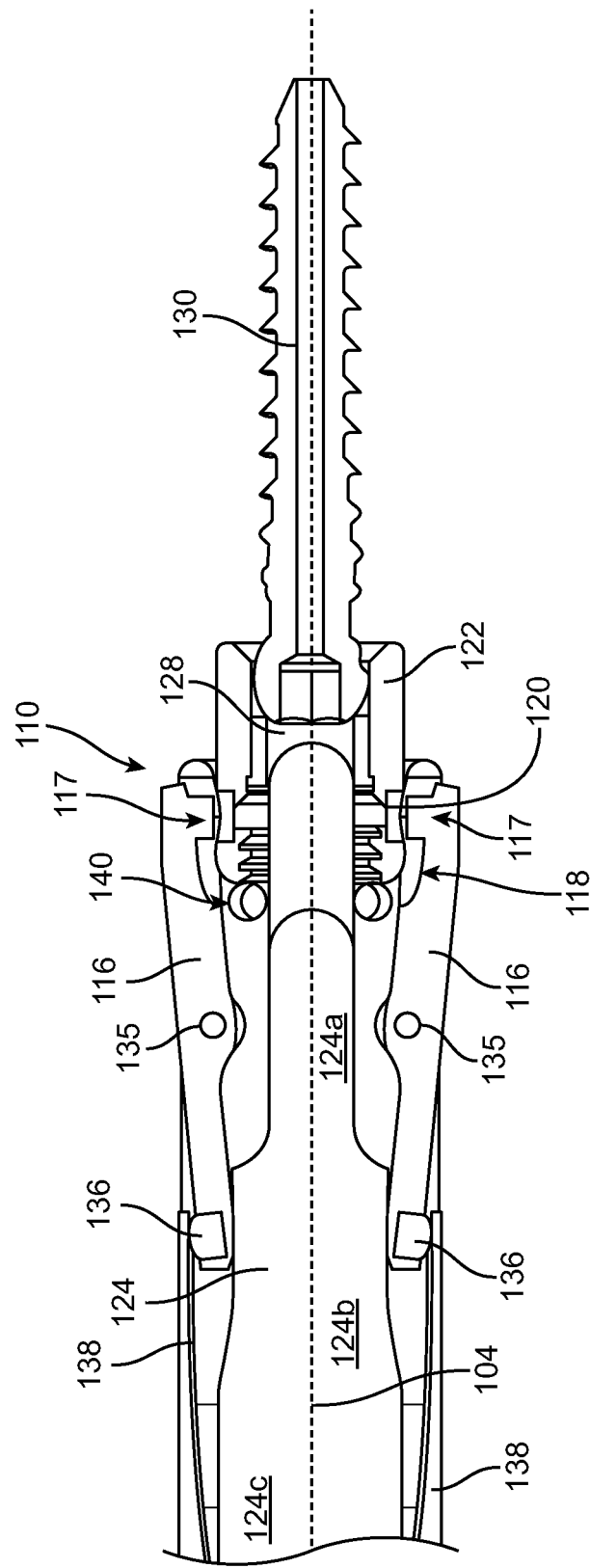
FIG. 3A is a cross-sectional view of the distal end of the apparatus in FIG. 1 looking generally into the plane and in the direction of the arrows formed by the lines III in FIG. 2.
Figure 3B:
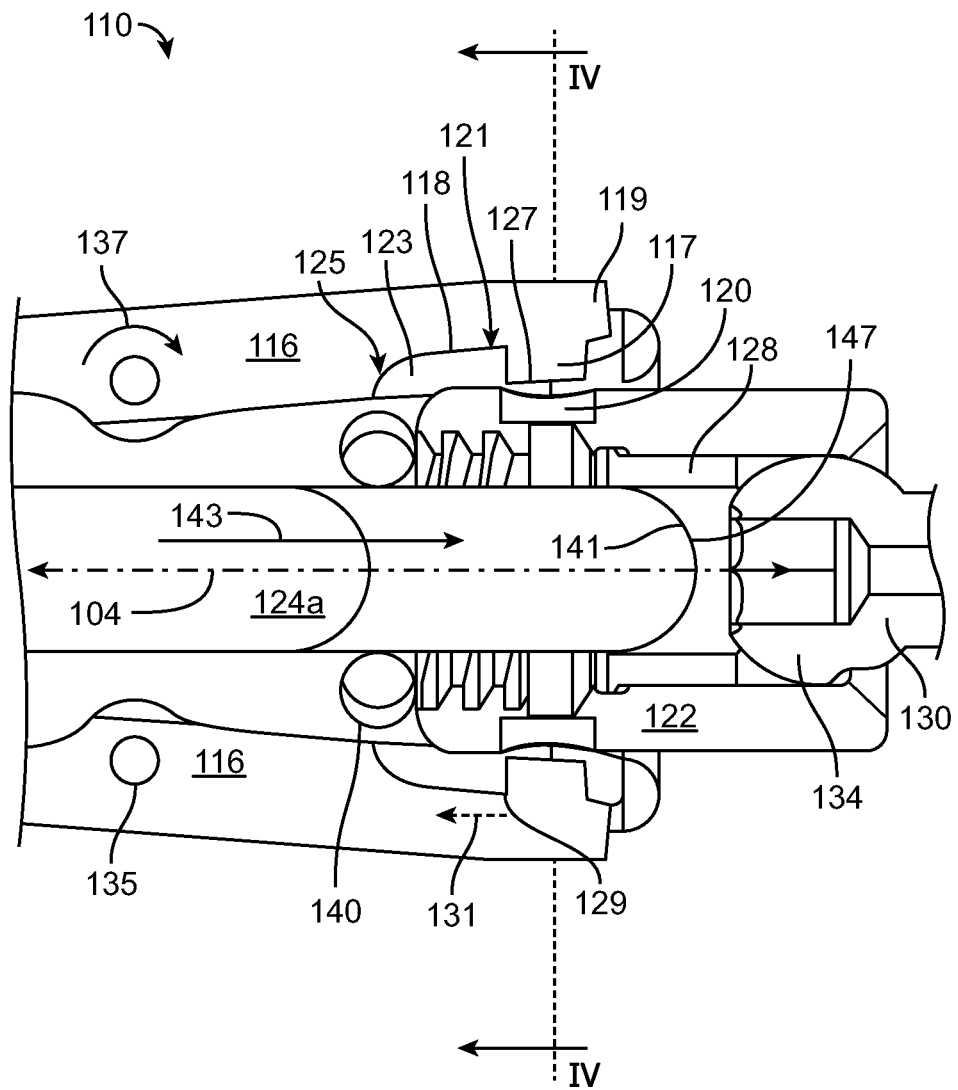
FIG. 3B is an enlarged cross-sectional view of the apparatus of FIG. 1, looking generally into the plane and in the direction of the arrows formed by the lines III in FIG. 2.

As shown in FIGS. 3A-3B, the barrel body 102 includes the inner shaft 124 disposed within the barrel body 102. The inner shaft 124 is operably coupled to the lever 112. The inner shaft 124 may be slidably disposed within the barrel body 102 and extends longitudinally from the proximal end of the lever 112 to the distal end 110 to the barrel body 102, such that the inner shaft 124 may be longitudinally displaced within the barrel body 102 by rotation of the lever 112 about the trigger pin 106. The proximal end of the inner shaft 124 is operably coupled to the proximal end of the lever 112 by way of a pin or a plate to displace the inner shaft 124 along the longitudinal axis 104. The lever 112 may extend downwardly from the trigger pin 106 and the barrel body 102 at an angled inclination, as shown in FIG. 1. The lever 112 may assume any polygonal shape having a distal end that can be longitudinally displaced. The trigger pin 106 and the lever 112 may be made from any suitable material as known in the art including, by way of example and not limitation, stainless steel, a thermoplastic or other materials. In some embodiments, the lever 112 and the trigger pin 106 may be associated with a locking and/or moving mechanism at the proximal end 108, for example, a ratcheting mechanism, for incrementally locking and/or distally moving the inner shaft 124 towards the distal end 110 and subsequently releasing the inner shaft 124 to be moved towards the proximal end 108 of the barrel body 102. Alternative spring locked or spring hinged mechanisms may be coupled to the trigger pin 106 and the lever 112 to move the inner shaft 124 distally and proximally within the barrel body 102.

As shown in FIGS. 3A-3B, in one embodiment, a protrusion 117 radially extends from an interior surface 118 of each of the tangs 116 proximate to a distal end 119 of the tangs 116. The protrusion 117 defines a distal end 121 of a groove 123 that may include a tapered proximal end 125. The protrusion 117 is adapted to engage a body pocket 120 (See also FIG. 5) disposed on the screw body member 122. The distal end 121 of the groove 123 includes a generally right angled corner 129 that is well suited for engaging the body pocket 120, locking the body pocket 120 into the distal end 110 of the barrel body 102, and applying a proximally directed force thereto, as indicated by arrow 131 in FIG. 3B. As such, the screw body member 122 may be locked in the distal end 110 of the barrel body 102.

In one embodiment, the protrusion 117 may include an interior surface 127 that may be the same general shape as the body pocket 120 to facilitate engagement of the body pocket 120 by the protrusion 117, as shown in FIG. 3B. For example, the protrusion 117 may have an interior surface 127 that is generally elliptical like the body pocket 120 illustrated in FIG. 5. However, the interior surface 127 may have any shape as desired to facilitate engagement of body pockets 120 having other shapes, including by way of example and not limitation, a circle, a rectangle, a pentagram, a hexagram, any regular polygon, any irregular polygon, and the like.

In one embodiment, the tangs 116 are operably attached to the distal end 110 of the barrel body 102 via pins 135 that act as hinge points around which the tangs may axially rotate, as illustrated by arrow 137 in FIG. 3B. The tangs 116 may be removable disposed/attachable in order to attach pairs of tangs 116 having protrusions 117 that are able to engage screw body pockets 120 having different shapes and/or sizes. The tangs 116 may include a cross-sectional shape looking along the longitudinal axis 104 that such that the interior surface 118 of the distal portion of each tang 116 is complementary to a peripheral surface of the screw body member 122 so as to secure the peripheral surface of the screw body member 122 relative to the tangs 116.

As shown in FIG. 3A, in one embodiment, the inner shaft 124 includes a stepped cross-section, such that a distal portion 124a includes a smaller diameter than a middle portion 124b, and the middle portion 124b includes a smaller diameter than a proximal portion 124c. The distal portion 124a is shown in both a first position, in which the inner shaft 124 has advanced distally and a second position, in which the inner shaft 124 has retracted proximally. The tangs 116 include a tip 136 on the proximal portion, which is operably coupled to a plurality of tensioned bars 138. The tensioned bars 138 may be formed as part of the barrel body 102 or may be operably coupled to the exterior portion of the barrel body 102. The tensioned bars 138 are pre-stressed such that the tensioned bars 138 displace the tip 136 and the proximal portion of the tangs 116 towards the longitudinal axis 104 when the inner shaft 124 is not engaged with the tips 136. The proximal portion of the tangs 116, and the distal portion of the tangs 116 and the protrusions 117 are displaced away from the longitudinal axis 104 by rotation about the pins 135 as the inner shaft 124 advances towards the screw body member 122. Therefore, the bias of the tensioned bars 138 on the tip 136 and the proximal portion of the tangs 116 axially displace or rotate the distal portion of the tangs 116 and the protrusion 117 axially away from the longitudinal axis 104, as the tangs 116 rotate about the pins 135. The stepped cross-section of the inner shaft 124 is shaped such that the distal movement of the inner shaft 124 by the lever 112 engages the proximal portion of the tangs 116 and the tips 136 to axially displace the tips 136 away from the longitudinal axis 104 by the middle portion 124b and the proximal portion 124c abutting the tips 136.

As shown in FIGS. 3A-3B, in one embodiment, the middle portion 124b is abutting the tips 136 to axially displace the tips 136 away from the longitudinal axis 104 while rotating and axially displacing the protrusions 117 on the distal end of the tangs 116 axially towards the longitudinal axis 104. Further distal movement of the inner shaft 124 by the lever 112 engages the proximal portion of the tangs 116 and the tips 136 with the proximal portion 124c of the shaft 124 to axially displace the tips 136 away from the longitudinal axis 104. When the proximal portion 124c abuts the tips 136, the tips 136 are further displaced away from the longitudinal axis 104, which rotates the tangs 116 about the pins 135 to axially displace the protrusions 117 towards the longitudinal axis 104 and engage the screw body pockets 120, as illustrated by the line 137. As the proximal portion 124c remains engaged with the tips 136 to keep the protrusions 117 engaged with the screw body pockets 120, the distal portion 124a pushes a bushing 128 into the pedicle screw 130 to create a frictional lock. Releasing the lever 112 causes the inner shaft 124 to move proximally to disengage distal portion 124a from the bushing 128 and the pedicle screw 130, while the proximal portion 124c disengages from the tips 136 to rotate and axially displace the protrusions 117 axially away from the longitudinal axis 104 and disengage the screw body pockets 120. Further proximal movement of the inner shaft 124 by releasing the lever 112 disengages the middle portion 124b from the tips 136 to finally release the screw body pockets 120 and the screw body member 122.

Figure 4:
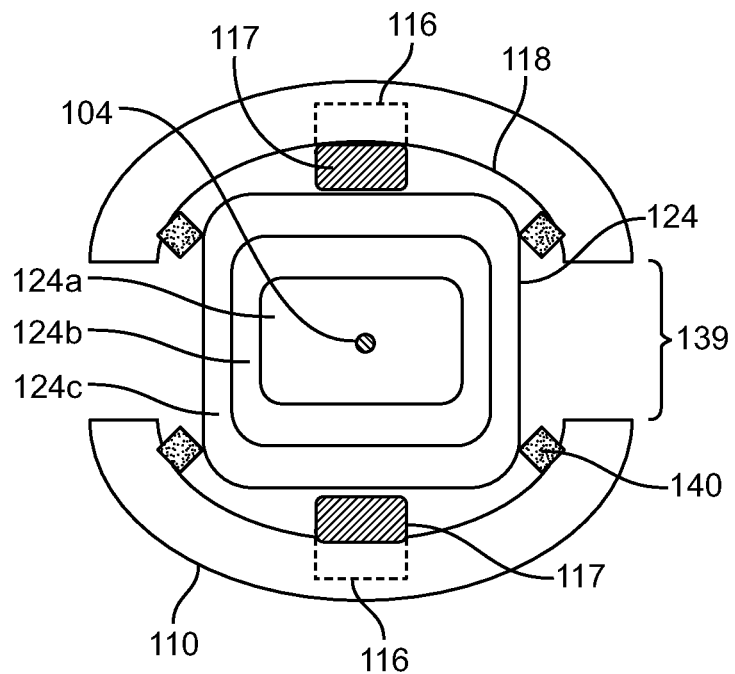
FIG. 4 is a cross-sectional view of the apparatus in FIG. 1, looking generally into the plane and in the direction of the arrows formed by the lines IV in FIG. 3B.

Referring to FIG. 4, for example, the tangs 116 may have a rectangular cross-sectional shape that is similarly shaped as the interior surface 141 of the screw body member 122 when the tangs 116 are engaged with the screw body member 122. Such a configuration of the interior surface 118 of the tangs 116 enhances engagement between the tangs 116 and the screw body member 122 and/or provides enhanced support against the screw body member 122 moving with respect to the tangs 116 when engaged by the tangs 116. Examples of screw body members 122 that may be useful in the current invention may be found in Purcell et al. U.S. Patent Application Publication No. 2008/0243189 and Purcell et al. U.S. Pat.

No. 7,377,923, both of which are hereby incorporated by reference in their entirety herein.

Also shown in FIG. 4 is the generally stepped profile of the inner shaft 124, whereby the distal portion 124a includes a smaller diameter than the middle portion 124b, and the middle portion 124b includes a smaller diameter than proximal portion 124c. Although the inner shaft 124 is generally shown to have rounded rectangular cross-sections, alternative configurations for the cross-section of the inner shaft 124 may be used, for example, circular, square, elliptical, polygonal cross-sections, and the like configurations. Also shown are the plurality of tabs 140 extending radially away from the interior surface 118 of the distal end 110 of the barrel body. The distal end 110 may also include an opening 139, by which the inner shaft 124 may be seen by an operator moving distally to engage the screw body member 122.

Figure 5:
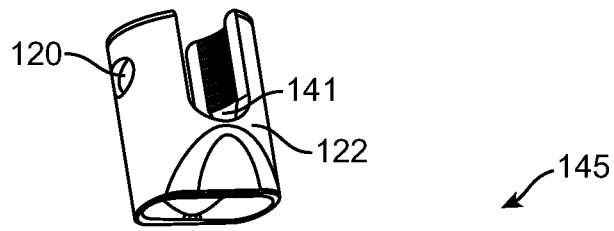
FIG. 5 is an exploded perspective view of an exemplary polyaxial pedicle screw for use with the apparatus according to the principles of the present disclosure.
Figure 5:
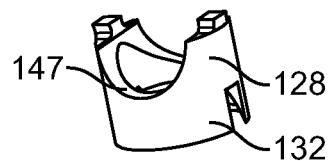
Figure 5:
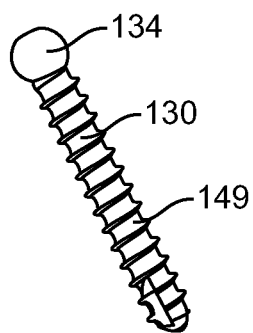

As shown in FIG. 5, a polyaxial pedicle screw assembly 145 comprises the screw body member 122, a bushing 128, and a polyaxial pedicle screw 130. The screw body member 122 is generally cylindrical in configuration and adapted to receive a fixed head portion 134 of the pedicle screw 130. The bushing 128 is adapted to fit within the screw body member 122 between the screw body member 122 and the head portion 134. In one embodiment, the bushing has a concave proximal surface 147 that is adapted to line up with an interior surface 141 of the screw body member 122 to accommodate a fixation rod (not shown). The bushing 128 has a slotted lower skirt portion 132 with tapered distal surfaces adapted to provide a press fitment about the head portion 134 of the pedicle screw 130. The pedicle screw 130 may include a substantially spherical or elliptical head portion 134 defining a slot therein used to drive a threaded shaft portion 149 of the screw 130 into a vertebra or other bone. Examples of bushings 128 and polyaxial pedicle screws 130 that may be useful in the current invention may be found in Purcell et al. U.S. Patent Application Publication No. 2008/0243189 and Purcell et al. U.S. Pat. No. 7,377,923, incorporated by reference herein.

In operation, the screw head locker 100 allows an operator to provisionally tighten the screw head portion 134 without inserting a rod and set screw into the pedicle screw. If the provisionally tightened screw needs to be adjusted, the screw may be loosened without the rod and set screw being re-inserted and then removed again.

The tangs 116 are movable between an open position and a closed position for engagement of the screw body pockets 120 upon lever 112 actuation, as noted hereinabove with regard to FIGS. 3A-3B. The tangs 116 are designed to secure the screw body member 122 to the screw head locker 100. The tangs 116 may be rotatably connected to the barrel body 102 by way of the pins 135. The tensioned bars 138 may bias the tangs 116 toward engagement with the inner shaft 124 at the tips 136 on the proximal portion of the tangs 116, as illustrated in FIGS. 3A-3B. The mechanical components may couple the inner shaft 124 and the barrel body 102 and, upon lever 112 actuation, displace the tangs 116 and distally move or slide the inner shaft 124 within the barrel body 102.

As shown in FIGS. 3-4, the inner shaft 124 is disposed between the tangs 116. Alternatively, the inner shaft 124 may be disposed within the barrel body 102 and between the tangs 116. The inner shaft 124 is generally rounded-rectangular in cross-section with a distal portion 124a that may be narrowed, rounded, or pointed to facilitate engagement with interior surfaces 141 and 147 of the screw body member 122 and the bushing 128, respectively. However, the inner shaft 124 may assume alternative shapes, such as circular, square, cylindrical, polygonal, and the like, having a distal portion 124a that accommodates entry into the screw body member 122 and to frictionally lock with the bushing 128. Alternatively, the inner shaft 124 may be any shape which may be customized for the particular barrel body 102 utilized. The inner shaft 124 may be made from any suitable material as known in the art including, by way of example and not limitation, stainless steel, a thermoplastic or other materials.

As illustrated by arrow 143 in FIG. 3B, actuation of the lever 112 longitudinally displaces the distal portion 124a of the inner shaft 124 towards the distal end 110 and causes the protrusions 117 of the tangs 116 to engage the body pockets 120. The longitudinal displacement of the inner shaft 124 is illustrated by the line 143 in FIG. 3B. Further actuation of the lever 112 displaces the distal portion 124a of the inner shaft 124 into the screw body member 122 and into engagement with the proximal surface 147 of the bushing 128 (as shown in FIG. 5), forcing the bushing 128 distally while the bushing 128 frictionally engages the screw head portion 134 of the screw 130. In one embodiment, the force exerted by the longitudinal displacement of the inner shaft 124 and the lower skirt portion 132 the bushing 128 on the pedicle screw 130 is distributed about the head portion 134 of the polyaxial pedicle screw 130 causing a frictional lock between the head 134 of the polyaxial pedicle screw 130 and the screw body member 122. Such a frictional lock effectively holds the screw body member 122 in a desired configuration relative to the polyaxial pedicle screw 130 for subsequent tightening of the screw 130 without the introduction of a fixation rod (not shown) into the screw body member 122.

Figure 6A:
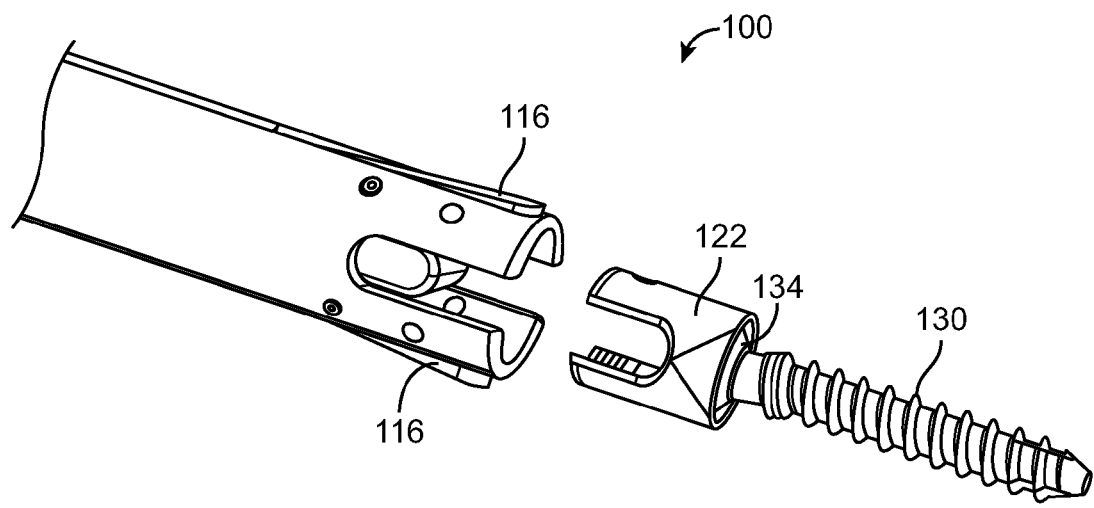
FIG. 6A is a perspective of the distal end of the apparatus with a coupler in an open release position in alignment with the polyaxial head of the bone screw in FIG. 5.
Figure 6B:
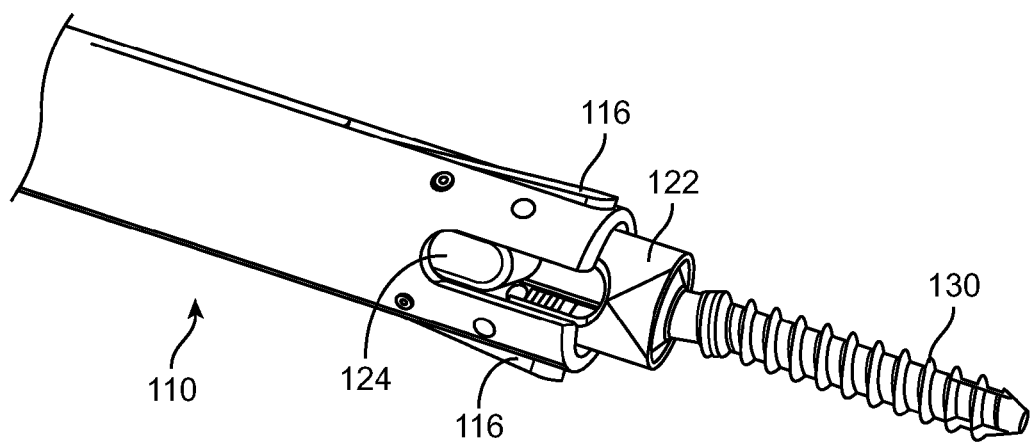
FIG. 6B is a perspective of the distal end of the apparatus with the coupler in the open release position engaged with the polyaxial head of the bone screw in FIG. 5.
Figure 6C:
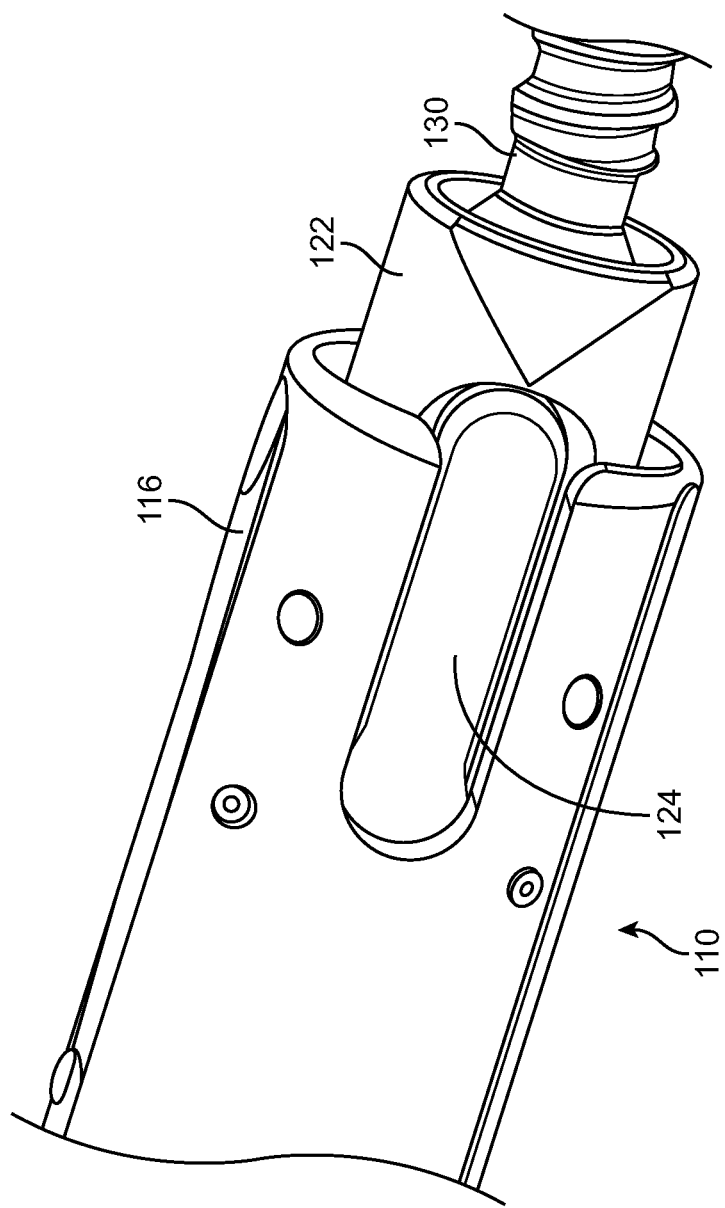
FIG. 6C is a perspective of the distal end of the apparatus with the coupler in a closed locked position with the polyaxial head of the bone screw in FIG. 5 and an inner shaft of the apparatus engaging a bushing within the polyaxial head.

In one embodiment of a method for locking the screw body member 122 to the head 134, in a first step the polyaxial pedicle screw 130 is assembled by inserting the threaded shaft portion 149 through the screw body member 122 with the head 134 being contained within the screw body member 122, as shown in FIG. 6A. The bushing 128 is then inserted into the screw body member 122 so that the proximal surfaces 141, 147 of the screw body member 122, and the bushing 128 align. The polyaxial pedicle screw 130 may also be pre-assembled. Next, the polyaxial pedicle screw 130 is driven into an insertion site such as a vertebra, as known in the art. Next, the screw body member 122 is oriented in the desired configuration by the medical professional, and with the screw body member 122 so oriented, the screw head locker 100 is aligned with the screw body member 122 such that the tangs 116 are positioned to accommodate the screw body pockets 120, as shown in FIG. 6B. Such an alignment is also illustrated by the cross-sectional view of FIGS. 3A-3B. The lever 112 is displaced, thereby actuating the inner shaft 124. Upon actuation, the inner shaft 124 is longitudinally displaced towards the distal end 110 of the barrel body 102. Actuation of the inner shaft 124 also causes the tangs 116 to engage the screw body pockets 120 by axial displacement towards the longitudinal axis 104, thereby securing the screw body member 122 to the distal end 110 of the screw head locker 100, as shown in FIG. 6C. In this embodiment, actuation of the inner shaft 124 couples with the tangs 116 to engage the screw body pockets 120. In another embodiment, actuation of the inner shaft 124 opens the tangs 116 to disengage from the screw body pockets 120.

Continued displacement of the lever 112 longitudinally displaces the inner shaft 124 into the screw body member 122 to contact the proximal surface 147 of the bushing 128, as shown in FIG. 3B. Further displacement of the lever 112 longitudinally displaces the inner shaft 124 distally against the bushing 128 and forces the body member 122 proximally to force the skirt 132 of the bushing 128 between the head portion 134 of the pedicle screw 130 and the screw body member 122 thereby creating a frictional lock therebetween.

Releasing the lever 112 causes the tangs 116 to disengage the screw body pockets 120 and the inner shaft 124 to longitudinally displace towards the proximal end 108 of the barrel body 102.

Referring now to FIGS. 3A, 3B, 6A, 6B, and 6C, the apparatus 100 is shown both engaged with and disengaged from the polyaxial head 122 of the bone screw 130. The inner shaft 124 moves between a first position and a second position in which the distal portion 124a, middle portion 124b, and proximal portion 124c each engage various portions of the tangs 116 and/or the polyaxial head 122. For example in the first position, the inner shaft 124 advances distally. The proximal portion 124c contacts the tips 136 on the proximal portion of the tangs 116. The larger diameter of the proximal portion 124c forces the tips 136 away from the longitudinal axis 104. The tangs 116 pivot about the pin 135 causing the protrusions 117 to engage the pockets 120 on the polyaxial head 122. The inner shaft 124 may continue to advance until the distal portion 124a engages the proximal surface 147 on the bushing 128. The distal portion 124a forces the bushing 128 into compressive/frictional contact between the polyaxial head 122 and the fixed head 134 of the screw 130.

In the second position, the inner shaft 124 retracts proximally. The proximal portion 124c gives way to the middle portions 124b which contacts the tips 136 and allows the tips 136 to return towards the longitudinal axis 104. The smaller diameter of the middle portion 124b allows the tips 136 to return towards the longitudinal axis 104. The tensioned bars 138 may bias the tips 136 towards the longitudinal axis 104. The tangs 116 pivot about the pin 135 causing the protrusions 117 to release from the pockets 120 on the polyaxial head 122. The inner shaft 124 may continue to retract until the distal portion 124a releases from the proximal surface 147 on the bushing 128. The apparatus 100 may then be removed from the polyaxial head 122.

A screw head locker for spinal immobilization systems is presented. The screw head locker includes a screw body member that is provisionally tightened before placing a rod or set screw into the screw body member. Such provisional tightening allows the screw body member to be frictionally locked at a specific angle relative to a polyaxial pedicle screw prior to rod or set screw introduction.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the screw head locker described herein and to teach the best mode of carrying out the same.

The invention claimed is:

1. An apparatus for provisionally locking a polyaxial head on a fixed head of a bone screw using a locking bushing, comprising:
   an elongated housing with a proximal end and a distal end, the distal end having couplers for releasably coupling with the polyaxial head, wherein the couplers include a pair of tangs with proximal tips and distal ends and are pivotably coupled about a midpoint to the distal end of the housing;
   an inner shaft slidably engaged within the housing and including a distal portion, a middle portion, and a proximal portion, wherein the distal portion includes a first diameter, the middle portion includes a second diameter greater than the first diameter, and the proximal portion includes a third diameter greater than the second diameter;
   a pair of tensioned bars that engage proximal tips of the couplers to bias the proximal tips towards the inner shaft and the distal ends away from the inner shaft; and
   an actuator that selectively positions the inner shaft within the housing to engage at least one of the distal portion, the middle portion, and the proximal portion with at least one of the couplers and the bushing disposed between the distal portion and the fixed head of the bone screw,
   wherein the actuator includes a lever pivotably coupled to the proximal end of the housing with a first end operably linked with the inner shaft and a second end with a handle.

2. The apparatus of claim 1, wherein the actuator positions the inner shaft in a first position to engage the proximal portion with the proximal tips of the couplers to cause the proximal tips to rotate away from the inner shaft and the distal ends of the couplers to rotate towards and to lock with the polyaxial head.

3. The apparatus of claim 2, wherein the actuator positions the inner shaft in a second position to allow the tensions bars to bias the proximal tips into engagement with the middle portion and release the polyaxial head from the distal end of the couplers.

4. The apparatus of claim 2, wherein the distal portion simultaneously engages the locking bushing in the first position.

5. The apparatus of claim 2, wherein the distal portion forces the bushing into frictional engagement between the fixed head of the screw and the polyaxial head.

6. The apparatus of claim 1, wherein distal ends of the couplers include protrusions extending towards the inner shaft configured to engage with mating pockets in the polyaxial head.

7. An apparatus for provisionally locking a polyaxial head on a fixed head of a bone screw using a locking bushing, comprising:
   a barrel with a proximal end and a distal end;
   one or more tangs pivotally coupled at a midpoint to the distal end of the barrel, each including a proximal tip and a distal tip having a protrusion for releasably coupling with a pocket in the polyaxial head;
   an inner shaft slidably engaged within the barrel and including a distal portion with a first diameter, a middle portion with a second diameter greater than the first diameter, and a proximal portion with a third diameter greater than the second diameter;
   one or more tensioned bars on the distal end of the barrel configured to bias each proximal tip of each tang towards the inner shaft; and
   an actuator that selectively positions the inner shaft within the barrel to engage at least one of the distal portion, the middle portion, and the proximal portion with at least one of the tangs and the bushing disposed between the distal portion and the fixed head of the bone screw, wherein the actuator comprises a lever pivotably coupled to the proximal end of the barrel with a first end operably linked with the inner shaft and a second end including a handle.

8. The apparatus of claim 7, wherein the actuator advances the inner shaft to engage the proximal portion with the proximal tip of the tang such that the proximal tip rotates away from the inner shaft and the distal tip rotates towards the polyaxial head to engage the protrusion with the pocket.

9. The apparatus of claim 8, wherein the actuator retracts the inner shaft to allow the tensioned bars to bias the proximal tips into engagement with the middle portion such that the distal tip releases the protrusion from the pocket.

10. The apparatus of claim 8, wherein the distal portion simultaneously engages a proximal surface of the bushing and forces the bushing to frictionally engage between the polyaxial head and the fixed head of the screw.

\* \* \* \* \*